US012048833B2

(12) United States Patent
Fech et al.

(10) Patent No.: US 12,048,833 B2
(45) Date of Patent: Jul. 30, 2024

(54) METHODS FOR INJECTING FLUIDS

(71) Applicant: Erbe Elektromedizin GmbH, Tuebingen (DE)

(72) Inventors: Andreas Fech, Tuebingen (DE); Klaus Fischer, Nagold (DE); Lars Blobel, Ammerbuch-Entringen (DE); Waldemar Wandel, Kusterdingen (DE); Markus Enderle, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1186 days.

(21) Appl. No.: 16/730,714

(22) Filed: Dec. 30, 2019

(65) Prior Publication Data

US 2020/0129700 A1 Apr. 30, 2020

Related U.S. Application Data

(62) Division of application No. 14/976,084, filed on Dec. 21, 2015, now Pat. No. 10,549,041.

(30) Foreign Application Priority Data

Dec. 29, 2014 (EP) .................................... 14200435

(51) Int. Cl.
*A61M 5/30* (2006.01)
*A61B 1/015* (2006.01)
(Continued)

(52) U.S. Cl.
CPC ........... *A61M 5/3007* (2013.01); *A61B 1/015* (2013.01); *A61B 17/3203* (2013.01);
(Continued)

(58) Field of Classification Search
CPC .............. A61M 5/3007; A61M 5/1407; A61M 5/16827; A61M 5/30; A61M 5/16809;
(Continued)

(56) References Cited

U.S. PATENT DOCUMENTS

| 5,312,332 A | 5/1994 | Bales et al. |
| 5,911,703 A * | 6/1999 | Slate ....................... A61M 5/30 |
| | | 604/68 |

(Continued)

FOREIGN PATENT DOCUMENTS

| CN | 101495045 A | 7/2009 |
| CN | 102974013 A | 3/2013 |

(Continued)

OTHER PUBLICATIONS

Chinese First Office Action dated on May 8, 2019, in corresponding Chinese Patent Application No. 201510883199.1, with English translation (22 pages).
(Continued)

*Primary Examiner* — Kevin C Sirmons
*Assistant Examiner* — Alexandra Lalonde
(74) *Attorney, Agent, or Firm* — Fitch, Even, Tabin & Flannery LLP

(57) ABSTRACT

An instrument head including an exit opening (23), a first feed line (11) for feeding a first fluid, a second feed line (12) for feeding a second fluid, and a reservoir (24) for storing the second fluid fed via the second feed line (12) is disclosed. The reservoir (24) is in fluid communication with the first feed line (11) and/or is adapted to be brought in fluid communication with the first feed line (11) via at least a valve (25) arranged in the instrument head, to deliver the second fluid stored in the reservoir (24) via the exit opening (23).

18 Claims, 13 Drawing Sheets

(51) Int. Cl.

| | | |
|---|---|---|
| *A61B 17/3203* | (2006.01) | |
| *A61M 5/14* | (2006.01) | |
| *A61M 5/168* | (2006.01) | |
| *A61M 5/20* | (2006.01) | |
| *A61M 39/22* | (2006.01) | |
| *A61M 39/24* | (2006.01) | |
| *A61M 5/178* | (2006.01) | |
| *A61M 5/19* | (2006.01) | |
| *A61M 5/31* | (2006.01) | |

(52) U.S. Cl.
CPC ...... *A61M 5/1407* (2013.01); *A61M 5/16827* (2013.01); *A61M 5/204* (2013.01); *A61M 5/2053* (2013.01); *A61M 5/2066* (2013.01); *A61M 5/30* (2013.01); *A61M 39/22* (2013.01); *A61M 39/24* (2013.01); *A61M 2005/1787* (2013.01); *A61M 5/19* (2013.01); *A61M 2005/3128* (2013.01); *A61M 2039/2473* (2013.01); *A61M 2205/50* (2013.01)

(58) Field of Classification Search
CPC .. A61M 5/2066; A61M 5/19; A61M 5/31596; A61M 5/1409; A61M 5/1408; A61M 5/2448; A61M 5/2053; A61M 39/22; A61M 39/24; A61M 2005/3128; A61M 2005/1787; A61M 2025/0073; A61M 2025/0089; A61M 2039/2473; A61M 5/204; A61M 5/00; A61M 5/142; A61M 5/3015; A61M 5/48; A61M 5/482; A61M 5/484; A61M 5/488; A61M 2005/3022; A61M 2039/242; A61M 2205/50; A61M 2205/33; A61M 2205/3331; A61M 2205/3334; A61M 2205/3337; A61M 2205/3344; A61M 2205/3351; A61M 2205/3355; A61M 1/00; A61M 1/77; A61M 1/774; A61M 1/782; A61M 3/0275; A61M 11/00; A61M 2210/1053; A61M 2210/106; A61M 2210/1064; A61M 5/14; A61M 5/145; A61M 5/168; A61M 5/16877; A61M 5/16881; A61M 2005/14513; A61M 2210/1042; A61M 2210/1046; A61M 2210/105; A61M 2210/1057; A61M 2210/1067; A61B 17/3203; A61B 2017/00154; A61B 2017/32032; A61B 1/015
See application file for complete search history.

(56) References Cited

U.S. PATENT DOCUMENTS

| | | | |
|---|---|---|---|
| 7,842,028 B2 | 11/2010 | Lee | |
| 2001/0027296 A1 | 10/2001 | McBeth et al. | |
| 2003/0216724 A1 | 11/2003 | Jahns | |
| 2006/0163506 A1 | 7/2006 | Cook et al. | |
| 2007/0049873 A1* | 3/2007 | Hansen | A61M 5/2425 604/187 |
| 2007/0089787 A1 | 4/2007 | Patzer | |
| 2008/0300611 A1* | 12/2008 | Houser | A61B 17/320068 606/167 |
| 2008/0314452 A1 | 12/2008 | Smith | |
| 2009/0236445 A1 | 9/2009 | Lintern et al. | |
| 2009/0281486 A1 | 11/2009 | Ducharme | |
| 2010/0160897 A1 | 6/2010 | Ducharme et al. | |
| 2011/0028887 A1* | 2/2011 | Fischer | A61B 17/3203 604/24 |
| 2011/0282381 A1 | 11/2011 | Cronin et al. | |
| 2012/0095435 A1* | 4/2012 | Hunter | A61M 5/3015 604/500 |
| 2013/0144207 A1* | 6/2013 | Gonon | A61M 5/30 604/70 |
| 2013/0325044 A1 | 12/2013 | Wang et al. | |
| 2013/0331772 A1 | 12/2013 | Vogt | |
| 2014/0039394 A1* | 2/2014 | Stockmar | A61M 5/3007 604/151 |
| 2014/0188050 A1 | 7/2014 | Dittrich | |
| 2014/0221987 A1 | 8/2014 | Jeong et al. | |
| 2014/0276534 A1* | 9/2014 | Wood | A61M 5/30 604/500 |
| 2015/0025493 A1 | 1/2015 | Eggert et al. | |
| 2015/0112252 A1 | 4/2015 | Eggert et al. | |
| 2015/0157809 A1* | 6/2015 | Park | A61M 5/31511 604/173 |
| 2015/0320942 A1 | 11/2015 | Laugere et al. | |
| 2016/0100747 A1 | 4/2016 | Nitsan et al. | |

FOREIGN PATENT DOCUMENTS

| | | |
|---|---|---|
| EP | 2283885 A1 | 2/2011 |
| JP | 2005523408 A | 8/2005 |
| JP | 2009513256 A | 4/2009 |
| JP | 2013526957 A | 6/2013 |
| JP | 2014519899 A | 8/2014 |
| JP | 2014530652 A | 11/2014 |
| JP | 2015501688 A | 1/2015 |
| JP | 2015516250 A | 6/2015 |
| JP | 2016508820 A | 3/2016 |
| JP | 2016525900 A | 9/2016 |
| WO | 2007050553 A1 | 5/2007 |
| WO | 2013076151 A1 | 5/2013 |
| WO | 2013171311 A1 | 11/2013 |
| WO | 2014137383 A1 | 9/2014 |
| WO | 2014191842 A2 | 12/2014 |

OTHER PUBLICATIONS

Japanese Office Action dated Mar. 6, 2018, for Japanese Application No. 2015-253647, with English translation (6 pages).
English translation of Japanese Office Action dated Apr. 4, 2017, in corresponding Japanese Application No. 2015-253647 (5 pages).
Japanese Search Report dated Mar. 13, 2017, in corresponding Japanese Application No. 2015-253647, with English translation (53 pages).
European Office Action dated Oct. 19, 2016, in corresponding European Application No. 14200435.7, with English translation (5 pages).
European Search Report dated Jun. 16, 2015, in corresponding European Application No. 14200435.7 (6 pages).

* cited by examiner

METHODS FOR INJECTING FLUIDS

RELATED APPLICATION(S)

This application is a division of U.S. patent application Ser. No. 14/976,084, filed Dec. 21, 2015, which claims the benefit of European Patent Application No. EP 14200435.7 filed Dec. 29, 2014. The contents of each of the foregoing applications are incorporated herein by reference as if fully rewritten herein.

TECHNICAL FIELD

Embodiments of the present invention relate to injection of fluids, and more particularly, instruments, systems, and methods for injection of liquids into biological tissue for treatment thereof.

BACKGROUND

Appropriate application instruments that are suitable for introducing substances or suspensions, in particular cells into a biological tissue have been know. US 2001/0027296 A1, for example, describes an application instrument that may acquire cells from a tissue for processing and subsequently return them back into the tissue.

The instrument of US 2011/0282381 A1 is essentially based on that an appropriate canal is already present in the tissue, for introducing the substances. Occasionally, an appropriate canal may be pricked with a tip. Provision of an appropriate canal results in significant damage of the tissue to be treated. Furthermore, with the described instrument, it is very difficult to accomplish extensive and homogenous distribution of the substance to be introduced.

Starting from US 2011/0282381 A1, it is thus the object of the present invention to provide an instrument head allowing for efficient introduction of substances into biological tissue. With this, it is intended minimal damage of the tissue to occur and to optimize positioning of the introduced substance. Furthermore, an extensive and homogenous distribution of the introduced substance is to be accomplished as far as possible, wherein the substance that for example may be cells is gently treated such that no damage of the substance occurs.

SUMMARY

In particular, the object will be solved by an instrument head comprising:
a. an exit opening,
b. a first feed line for feeding a first fluid,
c. a second feed line for feeding a second fluid,
d. a reservoir for storing the fluid fed via the second feed line,
wherein the reservoir is in fluid communication with the first feed line and/or is adapted to be brought in fluid communication with the first feed line via at least a valve that is arranged in the instrument head, to deliver fluid stored in the reservoir via the exit opening.

An application instrument for an endoscope ordinarily has an instrument handle at the proximal end, a preferably elastic shaft and an instrument head at the distal end. According to the invention, at least the instrument head is configured in a specific manner.

A gist of the invention resides in introducing, with maximum efficiency, the substances, in particular a (cell) suspension into the tissue by a hydro-surgical instrument. For this, the instrument head according to the invention comprises a reservoir that can temporarily store the substance until it will be applied via a nozzle. The distal arrangement (in the vicinity of the tip) of the reservoir results in that upon applying pressure onto the substance, the substance may more or less be delivered via a nozzle. In this respect, only very low loss of pressure occurs. Furthermore, exposure time for pressure will significantly be reduced. This results in that the substance may be applied with high pressure under minimal stress. During application of cells this results in a very high survival rate, thus being able to accomplish a promising treatment result.

Due to very low loss of pressure it is also possible to introduce the substance relatively deep into the tissue at low stress or with low damage. Application of the substance by way of a water jet applicator generally has the advantage that only very minor damage of the target tissue will occur and very good distribution of the substance may be accomplished.

Preferably, the instrument head according to the invention comprises the first feed line and the second feed line, wherein the feed lines bear different fluids. In one embodiment, the first fluid is a propellant and the second fluid is the substance or suspension to be applied. The second feed line may also be utilized to fill the reservoir with the substance. The propellant is introduced into the reservoir via the first feed line, so that the substance will be expelled therefrom. Introduction may be done by way of an existing fluid communication or through a valve. Preferably, this valve is arranged in close vicinity to the distal end.

In one embodiment, the at least one valve comprises at least a locking part for locking the first feed line from the reservoir. The locking part may serve for preventing the first feed line from being at least partially filled with fluid during introduction of the substance. It may thus be prevented that the "precious" substance will be lost. Preferably, the valve is formed such that, in a pressure-free state, the first feed line is locked from the reservoir. For example, the locking part or the valve membrane, respectively, may be formed of an elastomer. Preferably, it is a passive valve, so that the space required for arranging the valve is very low. This has the advantage that the instrument head may be very low in diameter.

In one embodiment, the at least one valve is a shuttle valve that either locks the first feed line or the second feed line from the reservoir. For this, the locking part may appropriately be accommodated. During application of the first fluid (for example of the propellant) the first fluid may thus be prevented from entering the second feed or the second feed line, respectively. In this way, unwanted mixing of the first and second fluid in the second feed line may be prevented (substance watering). Provision of the shuttle valve has the further advantage that the first fluid not only may be used as a propellant, but may also be employed for the manufacture of a tissue canal in the biological tissue. For example, the first fluid may first be applied in a pulsed manner in order to establish the canal. After that, the reservoir is filled with the second fluid, and is applied again by way of the first fluid.

In this design, the shuttle valve has the further advantage that the first fluid for the manufacture of the tissue canal may be driven with significantly higher pressure without damage of the substance to be applied to occur. The shuttle valve protects the substance from excessively high pressure, which occasionally may negatively affect the effect of the substance.

In one embodiment, the exit opening comprises a valve, in particular in the form of a flexible nozzle. A flexible nozzle body may be incorporated in the instrument head, such that predetermined pressing radially acts on the nozzle body, and in the initial state the nozzle opening is locked. If the pressure in the reservoir increases, e.g. due to feed of the second fluid, the nozzle body first gets slightly curved outwardly without the exit canal being opened. Thus, a set volume amount may be pre-dosed in the reservoir. In the following, the pre-dosed volume may be expelled by way of the first fluid. Preferably, the material hardness of the flexible nozzle is selected such that sufficient expansion is accomplished and thus accommodation of a pre-dosed volume in the reservoir is accomplished. For this, preferably a pressure not exceedingly high, for example larger than 20 bar, is required.

Finally, a flexible nozzle may also prevent the exit opening from getting clogged and may assure that the second and/or first fluid is applied with a specified minimal pressure.

In one embodiment, in the instrument head, another valve for preventing back flow of fluid is provided in the second feed line. This may be a check valve. Said second valve may serve for maintaining a preset pressure in the reservoir, for example after introduction of the second fluid. Furthermore, the second valve prevents the second fluid from running on, as soon as active introduction of the second fluid into the second feed line will be suppressed. In this way, precise dosage may be realized.

The above-mentioned object will further be solved by an application instrument for an endoscope, wherein the application instrument preferably comprises a shaft and an instrument handle in the vicinity of or at the proximal end of the shaft. The application instrument, at the proximal end of the flexible shaft, may be provided with the already described instrument head in one of the described embodiments.

Similar advantages to those already described in connection with the instrument head will arise.

In one embodiment, the shaft and/or the instrument has an external diameter (Ad) of less than 3 mm. With the configuration of the invention of the instrument head the object of the invention may be realized, wherein common dimensions of endoscopic instruments may be maintained.

In one embodiment, the application instrument comprises a venting device in or on the second feed line. The venting device may be formed for venting the second feed line. For this, a shuttle valve and, as necessary, another small reservoir may preferably be provided. A vent may as well be provided for preventing run on. The venting device allows venting at least part of the second feed line immediately after introduction of the second fluid. In this respect, the amount of the introduced second fluid may precisely be dosed. Furthermore, the venting device may enable very rapid reduction of pressure built up in the reservoir. With the application instrument according to the invention it is thus possible to pulsedly deliver the fluids, thus achieving very steep falling edge of the pulse. This is the requirement for pulsed delivery of the fluids and for rapid switching between the deliveries of first and/or second fluid. Furthermore, it also allows for very deliberate delivery of the fluids. For example, in this way dosage of the delivered fluids may be assured.

The instrument handle may at least comprise a regulating valve or control valve with a valve drive, so as to generate pulsed/sequential pressurizing of the first feed line and/or the second feed line. Said regulating valve facilitates pulsed fluid delivery. The regulating valve allows for defined pressurizing, wherein expansion of connection lines, for example between the application instrument and the supply system may remain unconsidered. In this respect, with the application instrument according to the invention, significantly superior results may be achieved. Said improved results will be achieved by the optimized form of the pulse and the steepness of the rising and falling edges, respectively.

The above-mentioned object will furthermore be solved by an application system. The application system preferably comprises an application instrument as described above. Moreover, the application system may comprise a supply system, which is in fluid communication at least with the first feed line.

The supply system may be formed to convey the first fluid into the first feed line within a series of conveying intervals. The supply system may also provide at least the first fluid with suitable pressure values. As to the application system, there are also similar advantages to those already described in connection with the application instrument.

The supply system may comprise the controller that controls at least one valve, for example the regulating valve already described, such that within an application time interval of less than 2 s, in particular less than 1 s:

the first fluid, within at least a first conveying interval, with a first pressure in the first feed line;
the second fluid within a second conveying interval following the first conveying interval with a second pressure in the second feed line; and
the first fluid within at least a third conveying interval with a third pressure, will be conveyed in the first feed line.

According to the invention the supply system may drive the first and/or second fluid such that the first and the second fluid are delivered within very short time, and are preferably alternatingly delivered. In a preferred embodiment, immediate conveying of the second fluid in the second feed line occurs only for filling the already described reservoir. Then, in the third conveying interval, the first fluid, which serves as a propellant for expelling the second fluid from the reservoir is conveyed again. The applied third pulse level (developing the third pressure) is also essential in that with which pressure the second fluid is outputted.

Utilization of the first fluid not only for exposing a tissue canal but also as a propellant may advantageously be employed in configuring the application instrument. For example, the first feed line may be configured significantly more pressure-resistant than the second feed line that is operated with a preferably significantly lower second pressure.

The application system may comprise a pump for conveying the first fluid and a medium separation device that is arranged and formed such that the first fluid drives the second fluid also in the second conveying interval. Preferably, the supply system is utilized for conveying the first and second fluid in the first and the second feed line, respectively. For this, in the supply system or between the application instrument and the supply system a medium separation device may be provided providing the second fluid and driven by the first fluid. Thus, finally in the timely delayed second conveying interval, conveying the first fluid may be essential to driving the second fluid.

Alternatively, the medium separation device may be formed as or may be replaced with, respectively, a second pump or fluid source, respectively. That means, conveying the second fluid into the already-described reservoir may be done independently of the first fluid.

The first pressure may be larger than the third pressure. Preferably, the first pressure is significantly larger than the third pressure, in particular by at least 30%. In one embodiment, the first pressure may be larger than the third pressure by at least 100% or even by at least 200%. Preferably, the first pressure is designed such that at least partial separation of the target tissue is possible. The first pressure serves for creating a canal for introducing the substance. In one embodiment, the first pressure ranges between 40 and 100 bar, in particular between 60 and 90 bar. Contrary to this, the third pressure may for example be in the range between 1 and 40 bar, in particular between 2 and 20 bar. Preferably, the third pressure is selected such that gentle introduction of the substance is assured. Furthermore, choice of the third pressure depends on how deep the substance is to be introduced into the tissue.

The above-mentioned object may furthermore be solved by way of a control process for the operation of supply system. According to the invention, the control process may comprise the following steps:
  activating a first fluid source such that a first fluid with a first pressure during a first conveying interval is delivered;
  activating a second fluid source, such that a second fluid during a second conveying interval with a second pressure in a reservoir, in particular a distal reservoir of an instrument, is delivered;
  activating the first fluid source such that the first fluid with a third pressure during a third conveying interval is introduced into the reservoir to deliver the second fluid via an exit opening.

Similar advantages to those already described in view of the supply system arise. The control process may be employed in the context of the already illustrated application system.

In one embodiment, the steps a through c may be performed within an application time interval of less than 2 s, in particular less than 1 s. In one embodiment, per second, a canal for introducing the substance is opened and an appropriate pulse for the delivery of the substance is emitted. According to the invention, it is possible that following opening of the canal several steps of substance-delivery will be performed. In this respect, per step a, the steps b and c may be repeated several times.

In one embodiment, this repetition is done at least three times within 2 s.

Furthermore, the previously mentioned object will be solved by way of a computer readable storage medium with instructions for the implementation of the described control process, if the instructions are executed on a computing unit.

In the following, the invention will be described by way of several illustrating examples. Wherein:

In the following description equal reference numbers will be used for equal parts.

DETAILED DESCRIPTION

Figure 1:
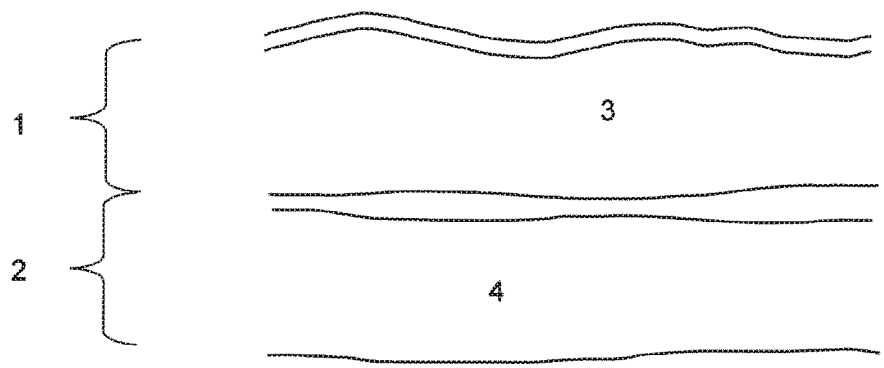
FIG. 1 is a schematic representation of the layered design of a hollow organ.

FIG. 1 shows a schematic representation of the layer design of a hollow organ of the efferent urinary tracts. Essential tissue layers are the mucosa 1 and the muscularis 2. The urinary tract is represented on the very top. This is followed by an epithelium that in turn is followed by the Lamina propria 3. In the following, the longitudinal muscle and circular muscle 4 are represented. The application system of the invention may be employed to assure faster regeneration of a sphincter defect of the represented urinary tract.

The application system allows for tissue-engineering-based therapy, in which a suspension, for example cells in a nutrient broth, is passed to the urethral sphincter muscle with sufficiently high survival rate of the cells through several tissue layers located upstream of the urethral sphincter muscle, and is deposited in the urethral sphincter muscle with the lowest loss possible. Ideally, in doing so, damage of the still intact sphincter muscle tissue is prevented. Hence, the circular muscle 4 from FIG. 1 represents a possible target tissue for the application system of the invention, wherein the applied water jet is required to first perforate the Mucosa 1 in order to transport the substance to the Muscularis 2.

There are numerous alternative applicabilities for the system of the invention, for example bile ducts, gastrointestinal walls, vessel walls, bronchial walls etc.

Figure 2A:
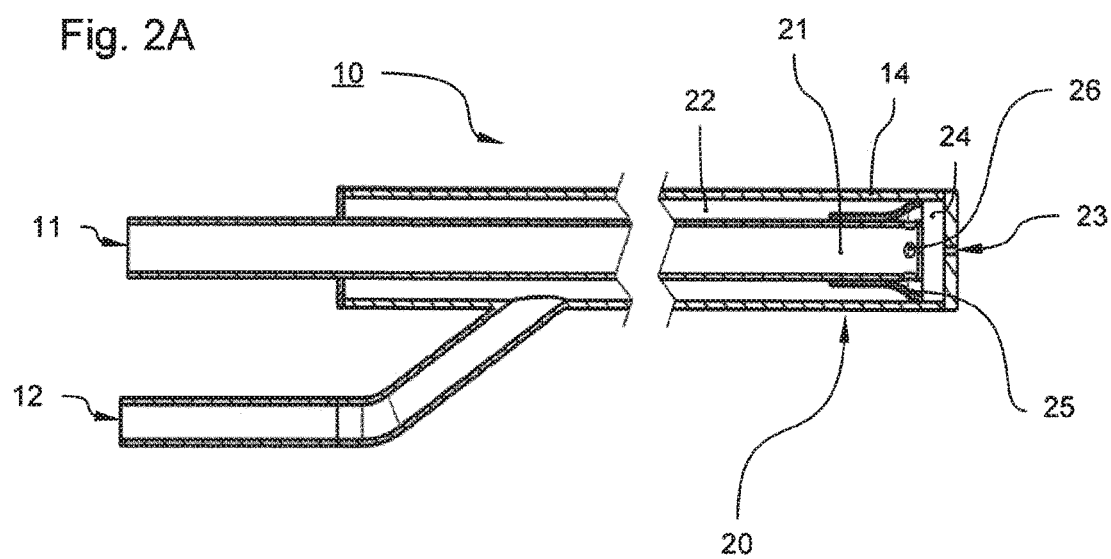
FIG. 2A is a schematic representation of an application instrument according to a first embodiment (shuttle valve only) with fluid flowing from an internal feed canal.

FIG. 2 shows a first illustrating example of an application instrument 10 according to the invention. An essential component of the application instrument 10 is the probe shaft 14, which preferably is at least partially flexible and proximally has an instrument head 20. This instrument head 20 has a nozzle 23 for the delivery of fluids. The fluids may be a saline or the already mentioned suspension with cell portions. In order to feed the fluids, an internal feed canal 21 is coaxially arranged in the lumen of the probe shaft 14. The external area of the internal feed canal 21 forms the external feed canal 22 surrounding the internal feed canal 21. The internal feed canal 21, as it is shown in FIG. 2A, is in fluid communication with a distal reservoir 24 via the lateral openings 26. A shuttle valve 25 arranged at the distal tip of the internal feed canal 21 allows for passing a first fluid from the internal canal 21 into the distal reservoir 24, and locks fluid communication between the distal reservoir 24 and the external feed canal 22.

The internal feed canal 21 is provided with the first and second fluid, respectively via a first inlet 11, and the external feed canal 22 via a second inlet 12.

Figure 2B:
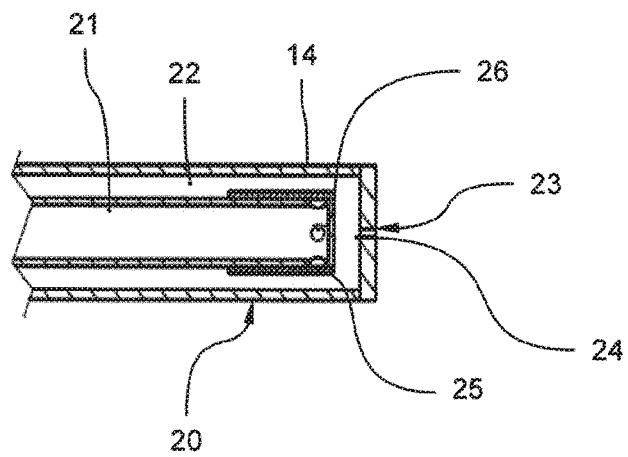
FIG. 2B is a schematic representation of the application instrument according to the first embodiment with fluid flowing from an external feed canal.

FIG. 2B shows a detailed view of the instrument head 20 from FIG. 2A. Contrary to the representation according to FIG. 2A, the shuttle valve 25 in FIG. 2B locks the lateral openings 26, so that immediate fluid communication between the distal reservoir 24 and the external feed canal 22 is established.

An aspect of the present invention is to deliver the fed fluids in an approximately perfect pulse shape via an exit opening 23, the nozzle 23. The instrument head 20 according to the invention allows delivery of fluid pulses at relatively low pressures, with which the fluids may suitably penetrate into the target tissue. Due to efficient utilization of the present pressures the cell will be "spared" in this application.

A further aspect of the invention is to introduce, by way of controlling the pulses, the fluids, in particular the cell suspension into different levels of the target tissues. Due to efficiently using the present pressures in the application, the cell suspension may be introduced into the target tissue "sparedly", in particular at different locations.

Figure 17:
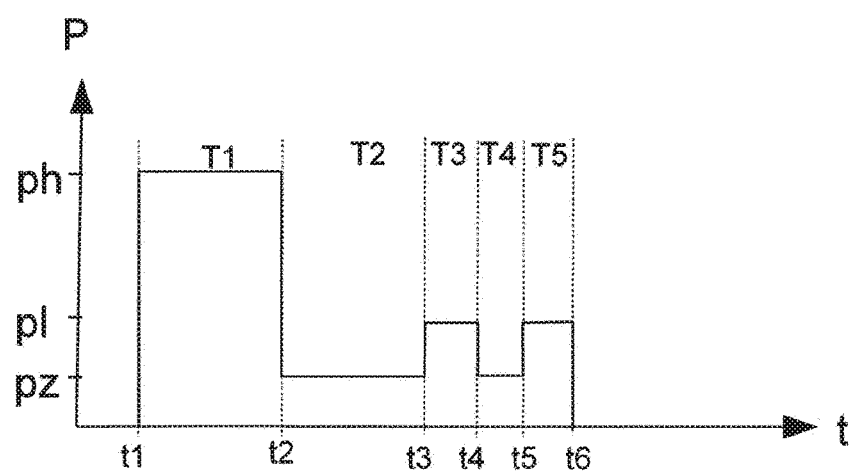
FIG. 17 is a pressure history generated by the supply system according to a first control algorithm.

For effectively introducing the suspension, within an application time interval, for example as it is shown in FIG. 17, the first fluid, within a first time interval T1, is first conveyed with high pressure ph. Within this first time interval T1 the instrument head 20 is in the state, such as it is shown in FIG. 2A. The first fluid exits the internal feed canal 21, fills the distal reservoir 24 and is delivered via the nozzle 23 with a defined nozzle diameter. Thus, the first fluid impinges on the tissue with high kinetic energy and may be utilized to create an introduction canal. In a second time interval T2 that follows, the second fluid is driven with a very low pressure pz so that the distal reservoir 24 becomes filled with the second fluid—i.e. the suspension. In this phase, the instrument head 20 may occupy the state such as it is shown in FIG. 2B. The shuttle valve 25 locks the internal feed canal 21 so that run on of the first fluid will be prevented. Following filling of the distal reservoir 24, in the third time interval T3 the first fluid is conveyed with a pressure pl. Preferably, this pressure pl is significantly lower than the high pressure ph so that gentle application of the suspension is done. In the third time interval T3, the instrument head 20 again is in the state a, such as it is shown in FIG. 2A. The first fluid penetrates into the distal reservoir 24 and displaces the second fluid. That is, the first fluid is a propellant and is for expelling the second fluid at a given pressure pz. According to the configuration, the distal reservoir 24 may be filled for another time in an application time interval (cf. fourth time interval T4) and the suspension may be delivered for another time (cf. time interval T5).

Figure 3A:
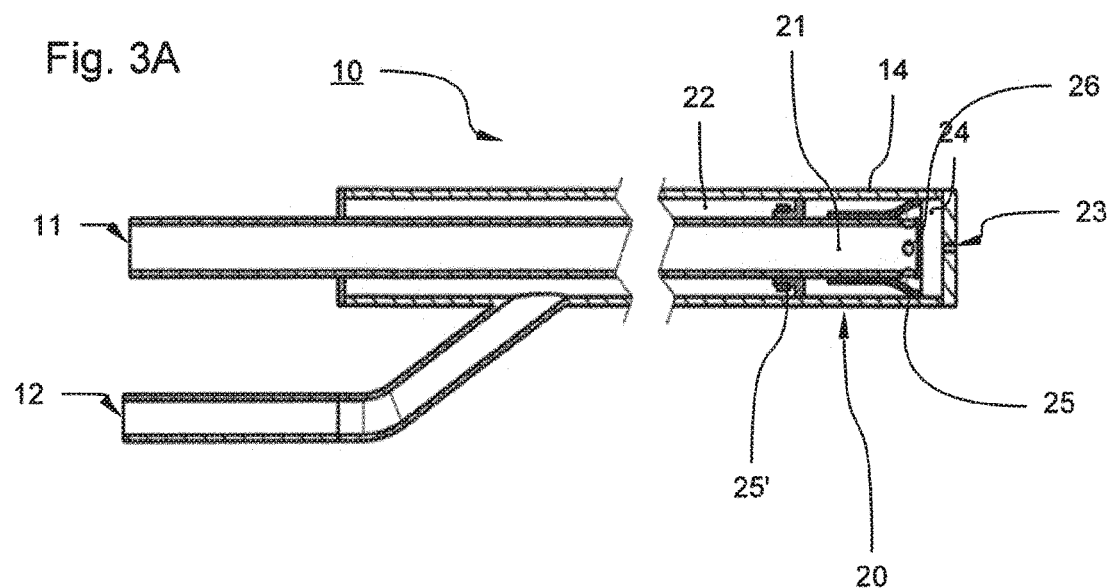
FIG. 3A is a schematic representation of an application instrument according to a second embodiment (shuttle valve with distal check valve) with fluid flowing from the internal feed canal.

FIG. 3A shows a further embodiment of the application instrument 10 according to the invention. Contrary to the embodiment of FIGS. 2A and 2B, in the embodiment according to FIG. 3A, another valve is provided in the instrument head 20. Said other valve, a check valve 25', as well as the shuttle valve 25, is located in the external feed canal 22. Opposite to the shuttle valve 25 the check valve 25' is arranged in lesser vicinity to the distal tip of the application instrument 10. The check valve 25' is a rubber lip that completely locks the external feed canal 22 in the pressure-free state. FIG. 3A shows a respective pressure-free state, in which the first fluid is conveyed and is outputted via the nozzle 23.

Figure 3B:
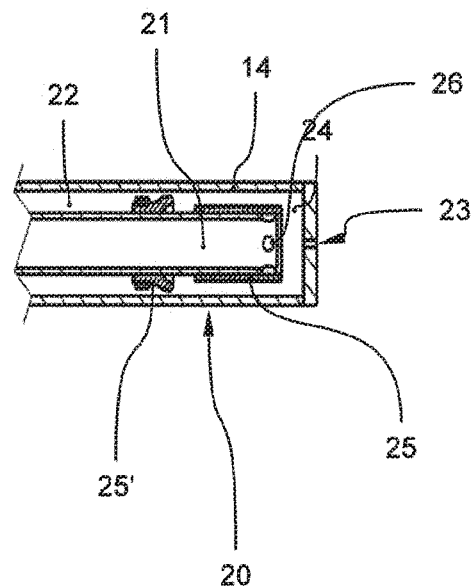
FIG. 3B is a schematic representation of the application instruments according to the second embodiment with fluid flowing from the external feed canal.

In conveying the second fluid via the second inlet in the external feed canal 22, the check valve 25' opens and, as already illustrated, the shuttle valve 25 locks the lateral openings 26. A corresponding state is shown in FIG. 3B. In this state, the distal reservoir 24 may be filled. As soon as the fluid flow in the external feed canal 22 stops, the check valve 25' closes. In this respect, the second fluid is prevented from running on. If in the internal feed canal 21, the pressure exceeds the pressure of the distal reservoir 24, the shuttle valve 25 opens. This may result in that a very steep external edge may energetically be created at the pulsed jet.

Figure 4A:
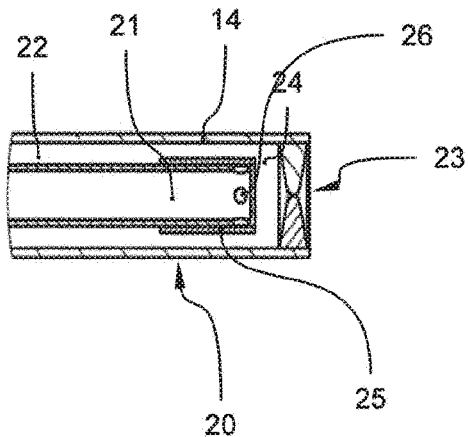
FIG. 4A is a schematic representation of an instrument head according to a third embodiment (a flexible nozzle) with fluid flowing from the external feed canal.
Figure 4B:
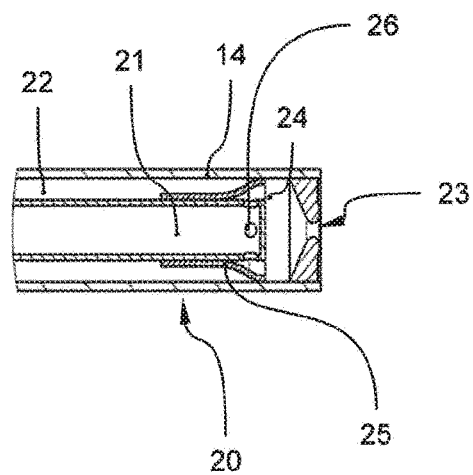
FIG. 4B is a schematic representation of the instrument head according to the third embodiment with fluid flowing from the internal feed canal.

The described embodiment allows to be employed in particular advantageously with a flexible nozzle 23, as it is exemplified in FIGS. 4A and 4B. However, the flexible nozzle 23 may also be of advantage, independent from a check valve 25' being present or not.

The flexible nozzle 23 according to FIG. 4A is closed in the pressure-free state. For this, the flexible nozzle body is incorporated into the application instrument 10 such that specific pressing radially acts on the nozzle body, locking the nozzle opening in the initial state. If the pressure proximal of the nozzle body in the distal reservoir 24 increases, for example due to feeding the second fluid, the nozzle body is first slightly bent outwards without the nozzle being opened (not shown). Thus, a defined volume amount in the distal reservoir 24 may be pre-dosed. Subsequently, the pre-dosed volume, such as already described, with a subsequent high pressure pulse (cf. third or fifth time interval T3, T5) may be introduced into the canal that is opened in the tissue. The nozzle body described in this illustrating example has a circumferential lip that tapers in the radial direction. The nozzle body may also be designed bisectionally. For example, the circumferential lip may consist of a flexible material, while, at its base, it is enclosed by a support of hard material. The performance of the flexible nozzle 23, in particular the expansion thereof, in the pre-dosing and filling phase, respectively, crucially depends on the choice of material and the extent of pressing in the incorporated state. According to the invention, the flexible nozzle 23 is configured such that sufficient expansion and thus accommodation of the pre-dosed volume in the distal reservoir 24 may be accomplished without the requirement of high pressure, for example higher than 20 bar. Moreover, the flexible nozzle is configured such that, in the open state, the nozzle opening 23 is large enough for a jet effect, i.e. sufficient acceleration of the fluid, to be allowed to be achieved.

The flexible nozzle 23 according to the invention may be employed for preventing run on of the fluid following application of the first and/or second fluid. Simultaneously, at appropriate filling of the distal reservoirs 24, a certain preliminary pressure is saved, which then may be retrieved. Moreover, the flexible nozzle 23 minimizes the risk of clogging the application instrument 10. In the configuration according to the invention, clogging only results in increase of pressure, which in turn causes expansion of the nozzle 23 such that polluting particles may pass.

FIG. 4B shows the instrument head 20 with the flexible nozzle 23 being open, for example within the third time interval T3.

Figure 5:
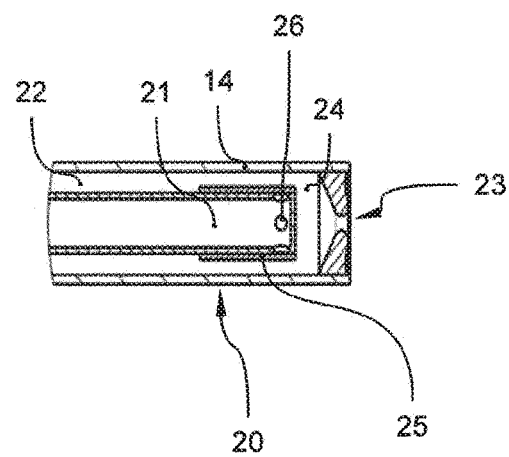
FIG. 5 is an instrument head of a fourth embodiment (also a flexible nozzle with cell suspension feed through the external feed canal)

FIG. 5 shows an alternative embodiment of the instrument head according to FIGS. 4A and 4B. Here, the external feed canal 22 is for feeding the first fluid, and the internal feed canal 21 is for feeding the second fluid. The state shown in FIG. 5 for example occurs in the first time interval T1 if the first fluid is used for creating a tissue canal. Also in the other embodiments already described, according to the invention, the internal feed canal 21 may be used for the second fluid, and the external feed canal 22 may be used for the first fluid.

Figure 6A:
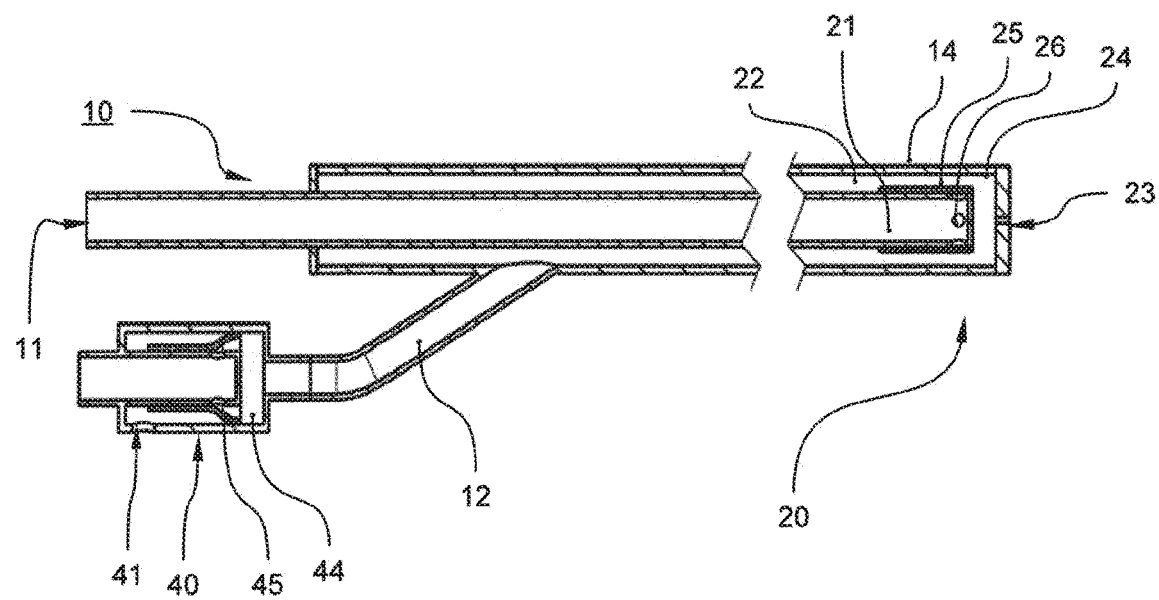
FIG. 6A is a schematic representation of an application instrument according to a fifth embodiment (venting device) with fluid flowing from the external feed canal.
Figure 6B:
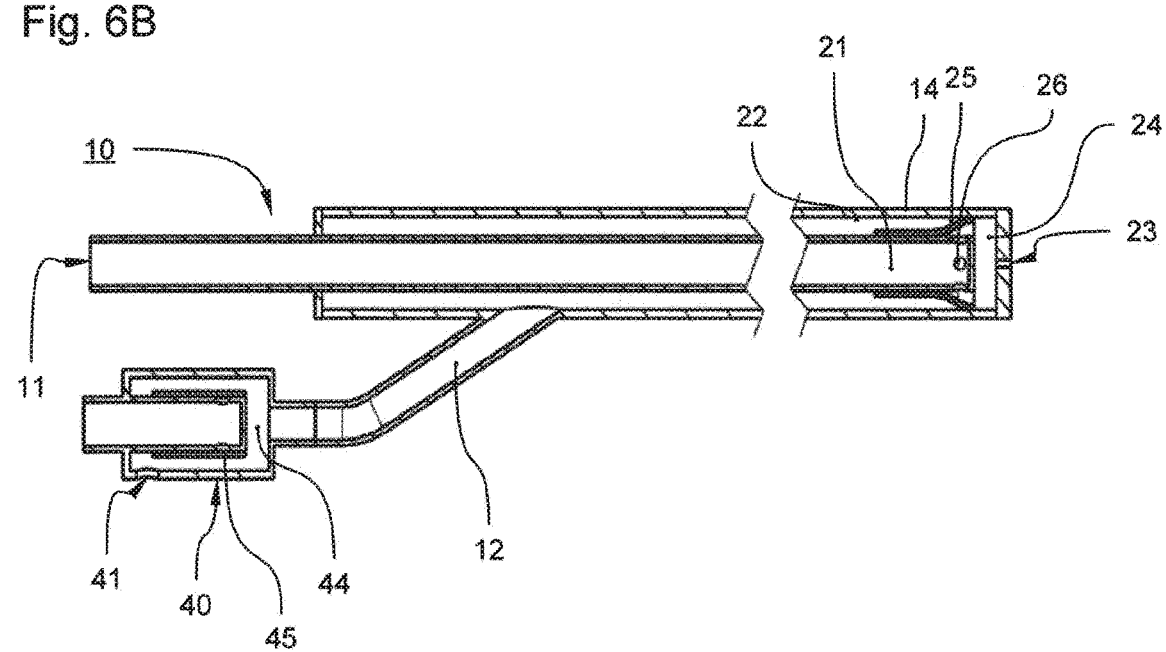
FIG. 6B is a schematic representation of the application instruments according to the fifth embodiment with fluid flowing from the internal feed canal.

FIGS. 6A and 6B show another illustrating example according to the invention, in which a flexible element is used as a second passive valve. Different from the illustrating example according to FIGS. 2A and 2B the application instrument 10 of FIG. 6A has a venting device 40 in the second inlet. An essential component of the venting device 40 is the venting chamber 44, in which the second inlet 12 ends, a vent 41 and a venting valve 45. The function of the vent 41 is controlled by way of the venting valve 45. The vent 41 allows venting the second inlet 12 and thus venting at least a section of the external feed canal 22. If the second inlet 12 is pressurized, the venting valve 45 locks after retrograde (sealing effect between the second inlet 12 and the vent 41). Distally from the venting valve 45 there is excess pressure in the venting chamber 44. Consequently, the second fluid may flow toward the instrument head and may be delivered (for example during the third time interval T3). This state is shown in FIG. 6A.

If the pressure in the second inlet 12 declines, the venting valve 45 is transferred into its initial state and locks the proximal portion of the second inlet 12 against the venting chamber 44 (cf. state according to FIG. 6B). Simultaneously, the excess pressure in the distal area of the second inlet 12 is rapidly reduced via the vent 41. This results in that run on out of the nozzle 23 is stopped very fast, and ideally is prevented, since flow resistance in the vent 41 is significantly lower than that in the nozzle 23. In this respect, the pressure edge of the delivered and pulsed fluid jet may very steeply decline. Since the shuttle valve 25, in this state, locks the external feed canal 22, only very low amounts of the second fluid escape through the vent 41. According to the invention, it is conceivable to provide an apparatus for receiving the substance exciting the vent and to occasionally recover the substance. It is understood that, according to the invention, several vents 41 may also be provided.

In another illustrating example, the venting valve 45 is not a passive one but is an active valve or a control valve, respectively. For example, in the handle 62 of the application instrument 10 a magnetic valve may be provided taking over the function of the venting valve 45. This magnetic valve may be controlled by supply system 50 (cf. FIG. 10).

Figure 7A:
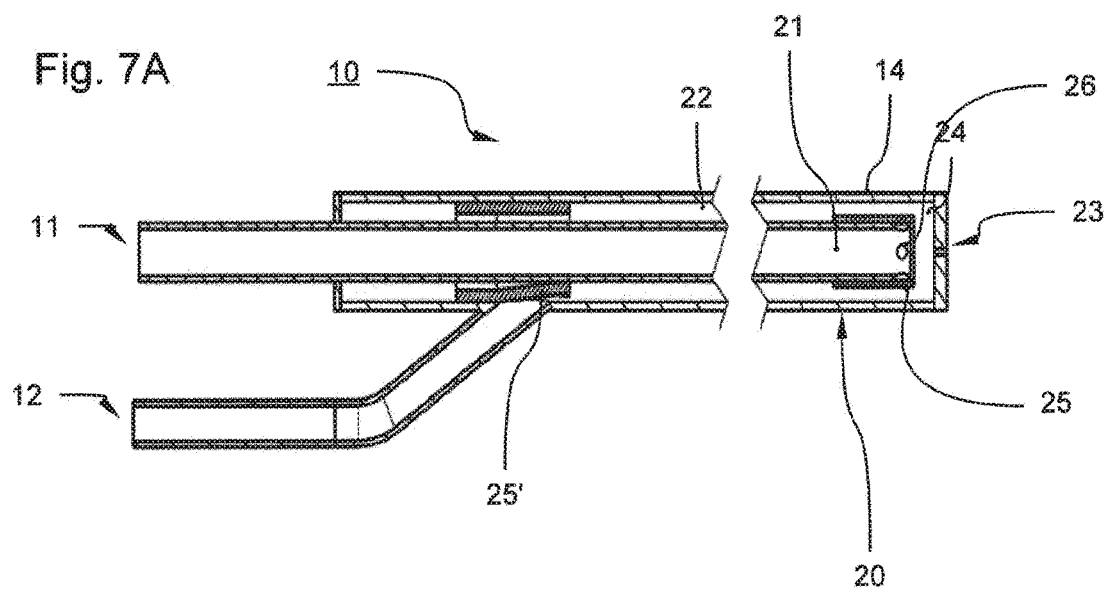
FIG. 7A is a schematic representation of an application instrument according to a sixth embodiment (shuttle valve with proximal check valve of a flexible element) with fluid flowing through the external feed canal.

FIG. 7A shows an embodiment of the application instrument 10, which in its mode of operation is similar to that of FIGS. 3A and 3B. The check valve 25' is formed by a flexible element at an orifice of the second inlet 12 leading into the external feed canal 22. The flexible element is designed such that, in a non-represented initial state, pressing to lock the second inlet 12 is provided. The strain accomplished therewith produces sealing effect in the pressureless state. If the second inlet 12 is pressurized, the flexible element deforms (cf. representation of FIG. 7A) such that it opens the fluid communication leading to the external feed canal 22. If the pressure in the second inlet 12 decreases again, the reset forces, after lower deviation of a specific pressure threshold, reset the flexible element into the initial state, and the check valve 25' closes.

Figure 7B:
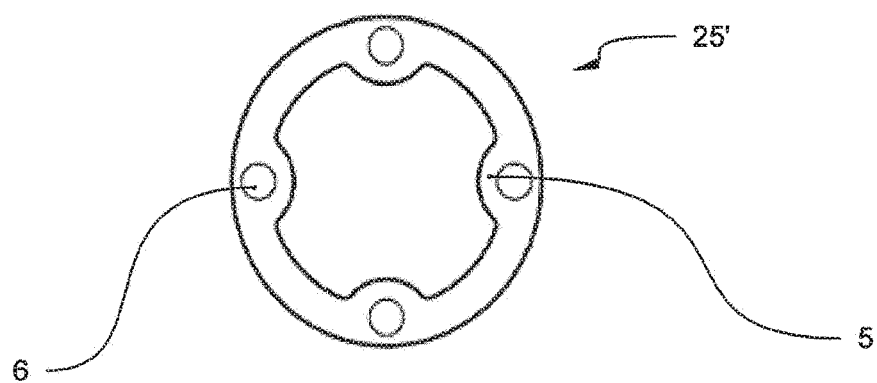
FIG. 7B is a detailed view of the flexible element from FIG. 7A.

In an illustrating example, the flexible element is composed of a flexible tubing section. By applying reinforcing structures, such as for example the ribs 5 shown in FIG. 7B extending in the direction of the longitudinal axis and/or reinforcing fibers 6 of a relatively stiff material, stronger pressing and consequently higher locking force of the check valve 25' may be accomplished.

Figure 8A:
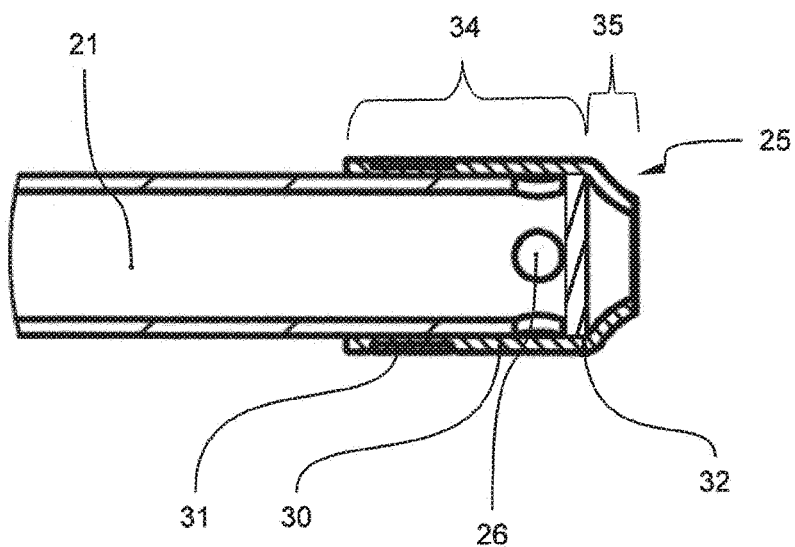
FIG. 8A is a schematic representation of a first alternative embodiment of a shuttle valve at the internal feed canal.
Figure 8B:
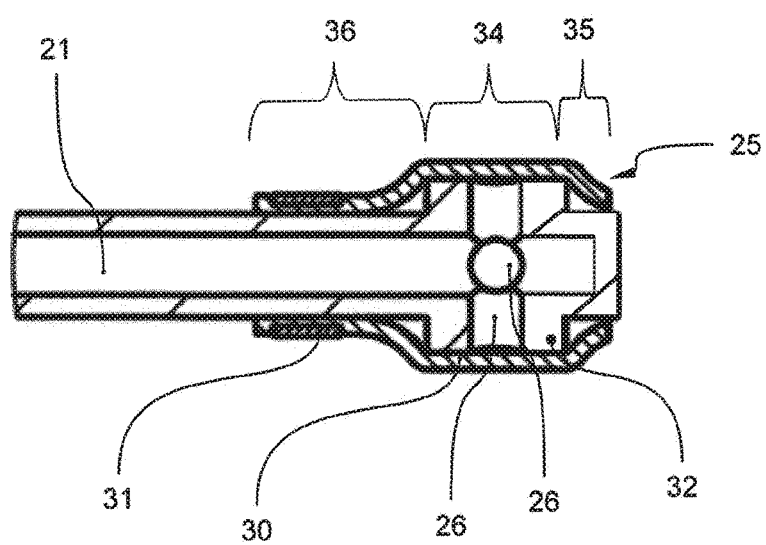
FIG. 8B is a schematic representation of a second alternative embodiment of a shuttle valve at the internal feed canal.
Figure 8C:
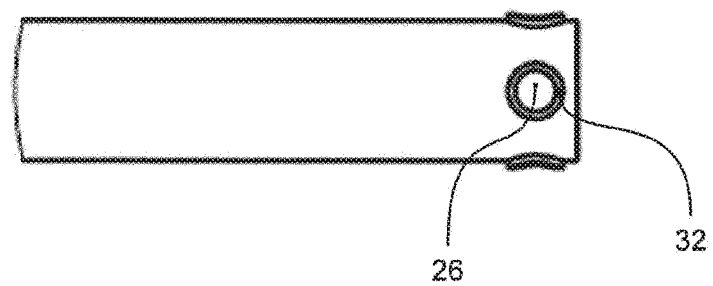
FIG. 8C is a schematic representation of a third alternative embodiment of the valve seat of the shuttle valve at the internal feed canal.

FIG. 8A, 8B, 8C show different embodiments of the shuttle valve 25. In a preferred embodiment, it is formed by a flexible material that is arranged at the outer side of the internal feed canal 21 thus locking the lateral openings 26 ending in it.

The embodiment according to FIG. 8A shows flexible tubing 30 that is arranged sectionwise over the distal end of the internal feed canal 21. Fixing of the flexible tubing 30 is done through a clamp ring 31. One significant aspect of the embodiment according to FIG. 8A resides in that the flexible tubing 30 partially projects over the distal end of the internal feed canal 21. Finally, a first section 34, to which the flexible tubing on the internal feed canal 21 abuts and a second section 35, in the course of which the flexible tubing 30 tapers, result. Accordingly, the flexible tubing 30 extends over a sealing edge 32 having exceptionally high surface pressure. In this way, a superior sealing effect is achieved.

In the embodiment according to FIG. 8B, the internal feed canal 21 sectionwise has a radial outwardly projecting bulge. This bulge is arranged at the location where the lateral openings 26 are located. Proximally and distally to the bulge, the internal feed canal 21 has a lower diameter. Consequently, in regard of the flexible tubing 30, a first section 34 with larger diameter, a second section 35 with low diameter and a third section 36 with low diameter result. The diameter of the second and third sections 35 and 36 may be identical. In another illustrating example (not represented) the diameter of the second and third sections 35 and 36 may also have different values. By way of different diameters of the first 34 and second 35 and/or third 36 sections a sealing edge 32 is created that increases the locking function of the shuttle valve 25. Furthermore, the larger diameter in the first section 34 causes preliminary extension and pre-tensioning of the flexible element, which also causes a superior sealing effect.

Higher surface pressure may also be achieved by the cylinder segments surrounding the lateral openings 26 of the internal feed canal 21 (cf. FIG. 8C). Finally, said cylinder segments also form sealing edges 32, which increase the locking function of the valve.

Figure 9A:
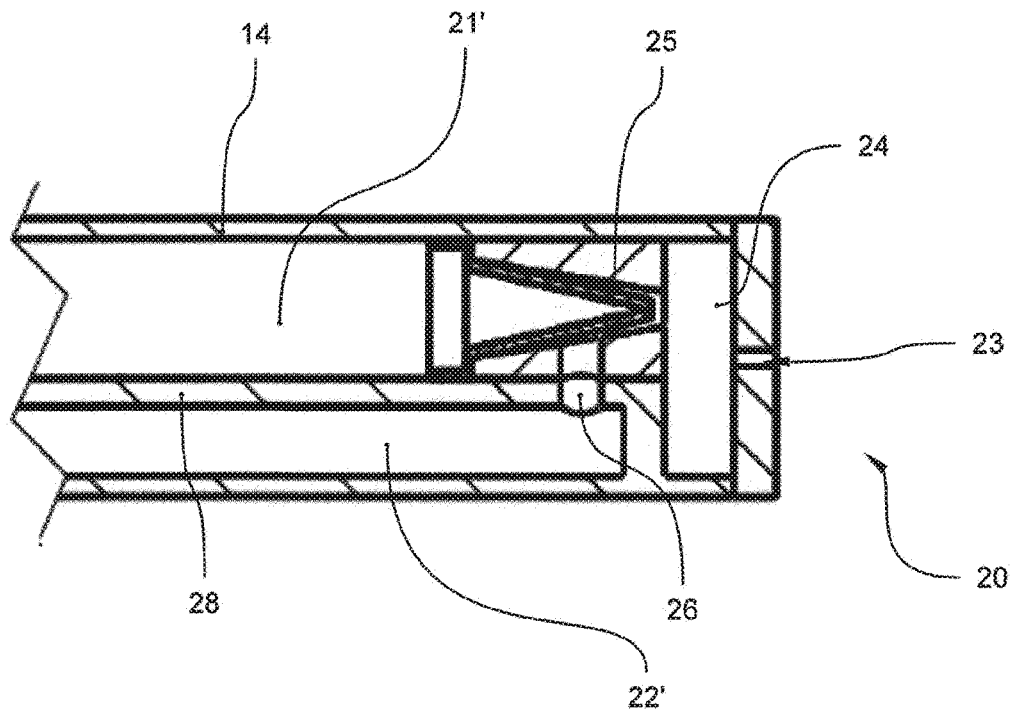
FIG. 9A is a schematic representation of an application instrument according to a seventh embodiment.
Figure 9B:
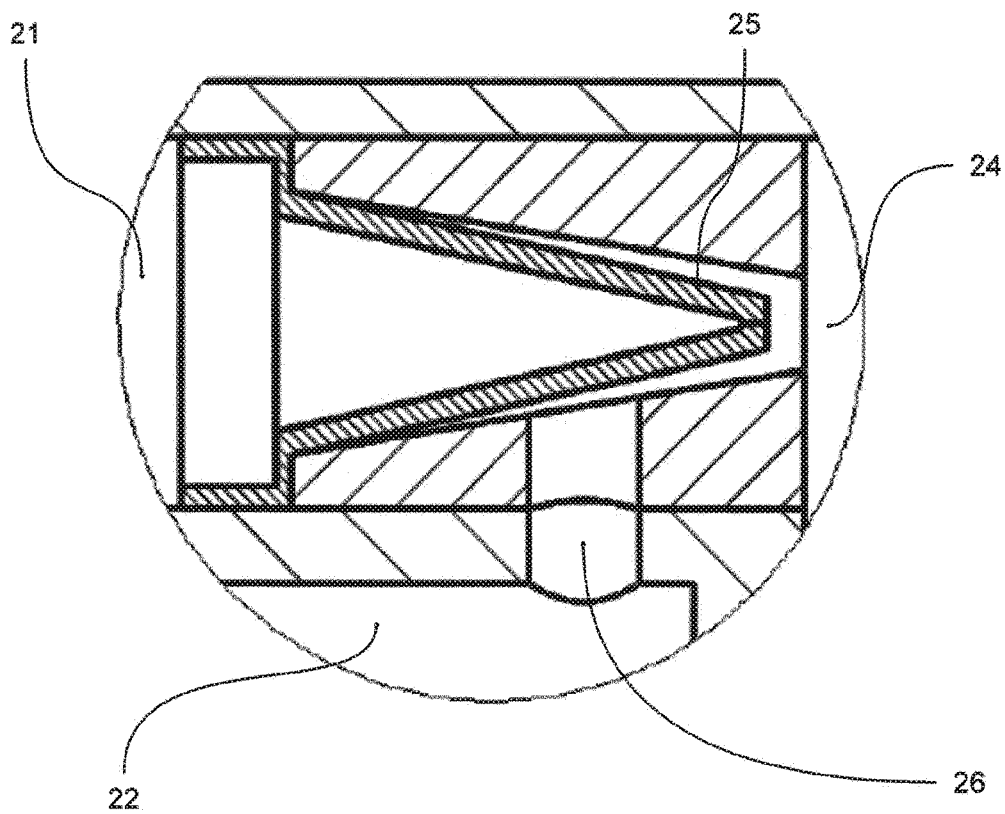
FIG. 9B is a detailed view of the instrument head according to FIG. 9A.

FIGS. 9A and 9B show further embodiments of the application instrument 10, in particular of the instrument head 20. Herein, the probe shaft 14 is a multi-lumen tubing (a two-lumen tubing is shown). Thus, in this illustrating example there are no canals that are coaxially arranged to each other, and comprising the internal feed canal 21 and the external feed canal 22. Instead, a first feed canal 21' for the first fluid extends parallel to a second feed canal 22'. Between the first inlet canal 21' and the second inlet canal 22' a separation wall 28 is provided. In the illustrating example shown, the cross section area of the first feed canal 21' is significantly different from that of the second feed canal 22'. For example, the first feed canal 21' may have a cross section area twice as large as that of the second feed canal 22'. These significantly differing cross section profiles may assure that different volume flows, e.g. different volumetric flow rates, (according to the invention the volume flow of the first fluid is larger than that of the second fluid) will be considered. According to the invention, the cross section profile of the first feed canal 21' may be more than twice as large as the cross section profile of the second feed canal 22'.

In the embodiment according to FIGS. 9A and 9B, the first feed canal 21' tapers at the distal end and then ends in a significantly broader distal reservoir 24 that is in immediate fluid communication with the nozzle 23. A side opening 26 of the second feed canal 22' laterally ends approximately in the middle of the tapering section of the first feed canal 21'. In the tapering section (=holder) a flexible element for forming a lip check valve 25 is arranged. Finally, a bidirectional valve results therefrom, which takes the function of the already described shuttle valve 25. The lip check valve is preferably axially mounted in the first feed canal 21' by the holder of a hard (non-flexible) material. The internal contour of the tapering section largely corresponds to the outer contour of the distal portion of the lip check valve. At this time, the opening of the tapering section is dimensioned such that, in the initial state (the flexible element is such as shown in FIG. 9A, i.e. not expanded) a gap results between the lips of the flexible element and the internal wall of the holder. For example, if the first fluid flows through the first inlet canal 21', the distal section of the flexible element—the lips of the valve—becomes expanded, so that it will be opened above a pressure threshold, and the first fluid may enter into the distal reservoir 24. Simultaneously, the lower valve lip is pressed against the wall of the tapering section by the pressure. Thus, the flexible element locks the side opening 26 from the second feed canal 22'. The pressure conditions of the first feed canal 21', in this state, are decoupled from the pressure conditions of the second feed canal 22'. If the pressure in the first feed canal 21' declines (for example after the first time interval T1), the shuttle valve 25 returns to the initial state, so that the side opening 26, as it is shown in the FIG. 9B, will be released. In the second time interval T2, the second fluid may pass through the gap almost unhamperedly, so that filling of the distal reservoir 24 at low pressure is possible. Since the flexible element now operates in the locking direction, it again acts as a barrier between the first feed canal 21' and the second feed canal 22'. Preferably, the gap is dimensioned such that the second fluid may unhamperedly flow at low pressure, and on the other hand the shuttle valve 25 is safely locked, so that to avoid entering of the second fluid into the first feed canal 21'.

The same effect (bidirectional valve effect) may also be achieved by the use of an internal acting valve in combination with a ball valve. Both valves are sequentially arranged in a lumen (preferably in the bigger one). Meanwhile, the ball valve is located proximal in relation to the flexible element. In this arrangement each one of the valves performs locking of the fluid in each one of the direction, while flow is unhamperedly maintained in each one of the other directions.

All the embodiments described so far have the object of the invention to accomplish different pressure levels in the first feed canal 21' and the internal feed canal 21, respectively, and the second feed canal 22' and the external feed canal 22 respectively. For this, the canals are decoupled from each other with the help of valves. At the same time, use of passive valves in the form described allows suppression of run on as well as realization of a pressure reservoir function. These two functions are in particular advantageous in combination with the use of proximally deployed active valves. In the following, several supply systems 50 of the invention for operating the described application instruments are described. According to the invention, the supply system 50 may also be used with other application instruments 10, for example common application instruments, to achieve the advantageous effects described below.

Figure 10:
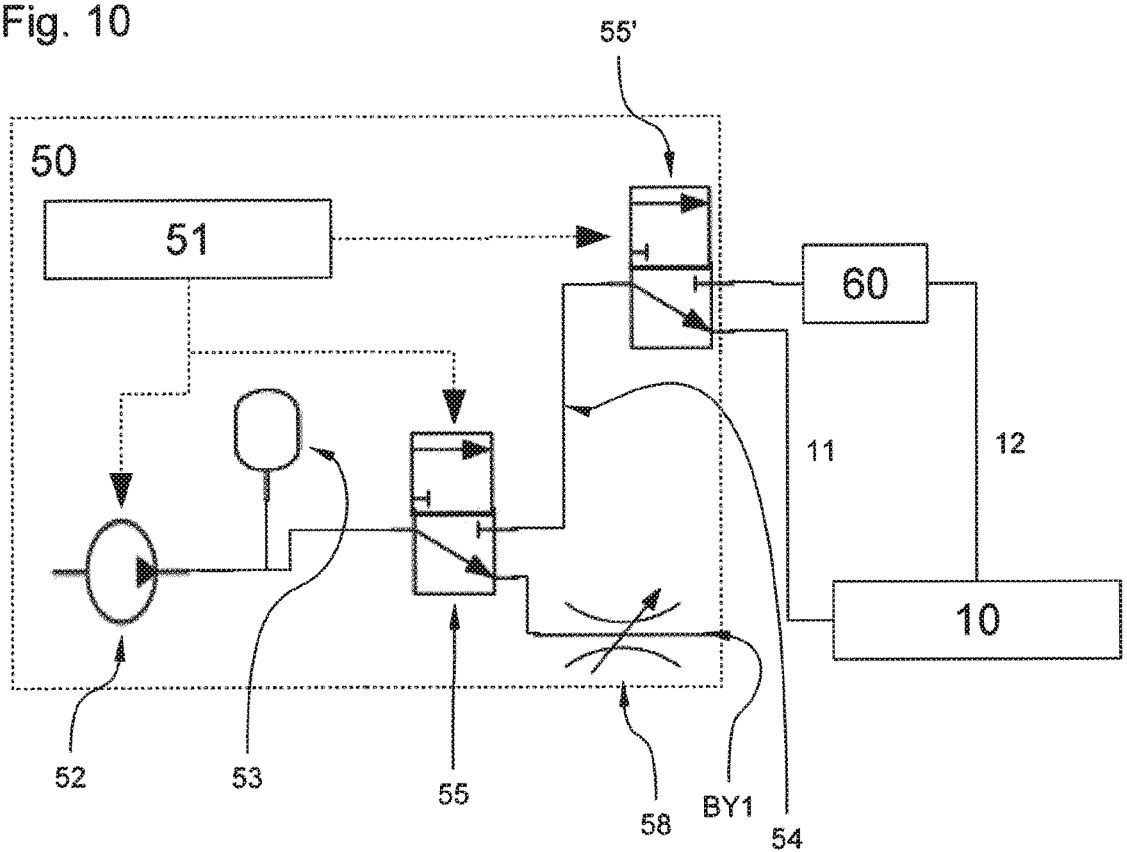
FIG. 10 is a schematic representation of a supply system according to a first illustrating example, wherein all control valves are incorporated in the supply system.

FIG. 10 shows supply system 50, through which the first inlet 11 and the second inlet 12 are connected to the described application instrument 10. In the illustrating example shown in FIG. 10, in the second inlet, a medium separation device 60 is provided, so that the supply system may deliver the first fluid, preferably saline, through different connections, wherein, depending on the selected inlet, different fluids may finally arrive at application instrument 10 (in the first inlet 11 the first fluid and in the second inlet 12 the second fluid).

The supply system 50 comprises a controller, which implements a control process, in which, within one application time interval, there are performed the steps of:

conveying the first fluid during the first conveying interval T1 with the high pressure ph into the first feed line 11;

indirectly conveying the second fluid during the second conveying interval T2 with the second pressure pz in the second feed line 12 while using the medium separation device 60; and conveying the first fluid during of the third conveying interval T3 with the third pressure pl in the first feed line.

According to the invention, the control process may be designed for additionally offering an appropriate control strategy during the fourth conveying interval T4 and the fifth conveying interval T5 (cf. FIG. 17).

For the realization of the control process the controller 51 interacts with a fluid source for example of a pump 52, a first control valve 55 and a second control valve 55'.

The pump 52 is in fluid communication with a pressure reservoir 53 of the supply system 50. In the illustrating example shown the pump 52 operates continuously and is flow-controlled. Control of the first control valve 55 which is in fluid communication with the pressure reservoir 53 allows setting a desired pulse shape (frequency, duty factor, effective pulse performance). Flow control of the pump causes constant volume flow of the first fluid within the supply system 50 independent of the switching position of the first control valve 55.

The first control valve 55 preferably is a 3/2-way valve, which, in the energized state, establishes fluid communication between the pressure reservoir 53 and a second control valve 55' via a pressure duct 54. The first control valve 55 essentially serves for building up a desired pressure level, whereas the second control valve 55' applies the set pressure level to the first inlet or the second inlet 12.

Under electroless condition (cf. representation according to FIG. 10) of the first control valve 55 there is a fluid communication between the pressure reservoir 53—and consequently also with the pump 52—and a first bypass duct BY1. The fluid flow is discharged via the bypass duct BY1 so that no illicit operating condition for the pump 52 will occur. Preferably, the first bypass duct BY1, as it is shown in FIG. 10, is provided with a with a throttle valve 58 that provides for a certain pressure level to be maintained in the upstream system section or the first control valve 55. For setting this pressure level, a hydraulic resistance at the throttle valve 58 may be set manually or via the controller 51 (cf. FIG. 13). In the illustrating example shown in FIG. 10 the resistance is preset. In the state shown in FIG. 10 in the pressure reservoir 53 a pressure level is set that is preset by the throttle valve 58. As soon as this pressure level is applied via the first control valve 55 to one of the two inlets 11, 12, the pressure in the respective inlet rebounds. In this respect, a fluid pulse with a steep edge may be emitted. According to the invention, it is thus possible, to attain a pressure level p'max during a bypass phase ÜD1, ÜD2 (cf. FIG. 19) that exceeds the desired pressure, for example the first pressure ph or the third pressure pl. Said pressures are preferably set via the efficiency of the pump 52. This pressure increase results in that the pressure pulse expands very fast in the lines. In this respect, a very steep pulse edge may be achieved at the nozzle 23. Furthermore, excess pressure may compensate loss of pressure in the inlets 11, 12. However, excess pressure must be selected such that fast increase of force is achieved, whereas the desired pressure at the nozzle 23 is not exceeded.

Starting from the first control valve 55, in the energized state (not shown) the pressure expands via the pressure ducts 54 to the second control valve 55'. In the illustrative example described, the second control valve 55' selects an inlet 11, 12.

In another illustrating example, the effect of excess pressure may be used to perform initial perforation of the biological tissue as a preliminary step for the following substance input. In this illustrating example, the supply system thus generates a steeply increasing pressure profile that declines with the time. The second control valve 55' is set such that during the course of the declining pressure edge, perforation of the tissue (first time interval T1) is performed first, and then filling of the distal reservoir 24 (second time interval T2) and finally input of the substance (third time interval T3) is performed.

Figure 11:
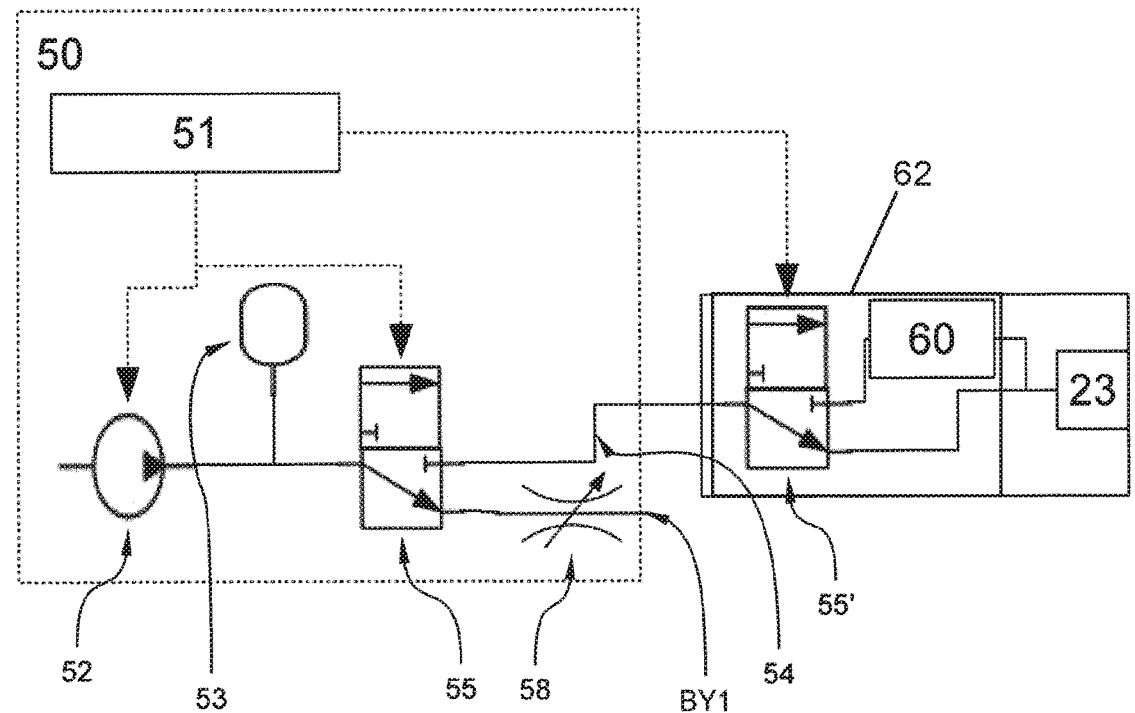
FIG. 11 is a schematic representation of a supply system according to a second illustrating example, wherein a control valve is incorporated in the application instrument.

In a further illustrating example (cf. FIG. 11), the second control valve 55' is integrated in the instrument 10. Preferably, control of the second control valve 55' is still done via the controller 51. In a further preferred illustrating example, the first control valve 55 is additionally incorporated into the application instrument as well. Preferably, respective incorporation in a handle 62 of the applicator instrument 10 is done. By this, the pressure pulses may be prevented from being attenuated through long and/or flexible feed lines. According to one aspect of the present invention, arrangement of the required control valves 55, 55' is as close as possible at or within the application instrument 10.

In one embodiment, the arrangement of the first control valve 55 is selected such that, in the electroless state, it locks communication between the pressure duct 54 and the pump 52. The pressure duct 54 is thus pressureless during the bypass phases ÜD1, ÜD2 or is pressurized with residual pressure, respectively. This arrangement has two advantages: On the one hand, the first control valve 55 is required to be energized only for a short time during activation for the delivery of a pulse sequence. On the other hand, the pressure level set by the throttle valve 58 is already available at the first pulse that is delivered.

Figure 12:
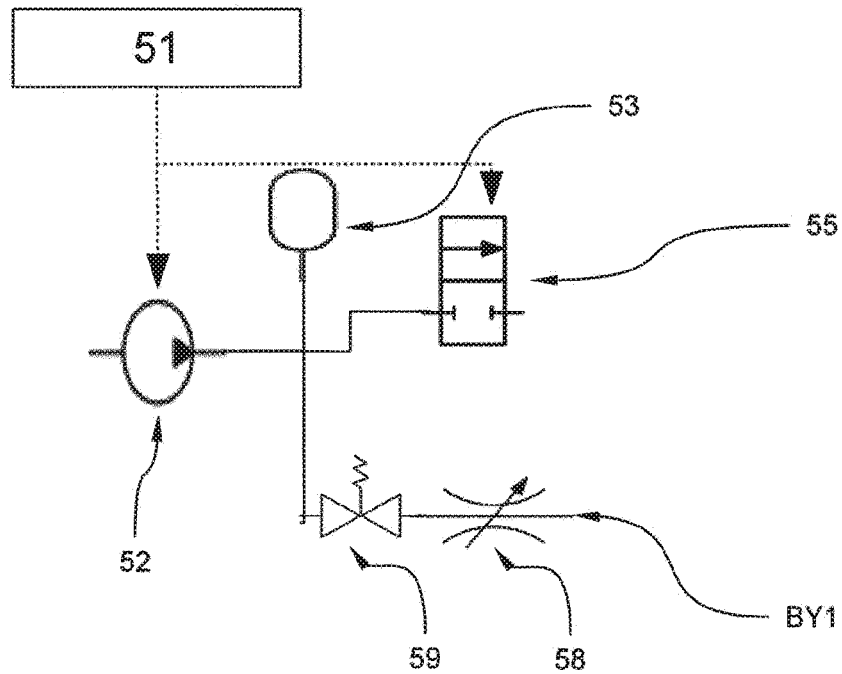
FIG. 12 is a schematic representation of a first alternative design for the creation of a pulsed water jet.

FIG. 12 represents another embodiment for effectively generating fluid pulses. In this embodiment, a 2-way valve is used as a first control valve 55. As in the above-described embodiment, there is fluid communication between the pump 52 and the pressure reservoir 53. Furthermore, there is fluid communication by way of a 2/2-way valve from the pressure reservoir to the first control valve 55.

Furthermore, there is fluid communication from the pressure reservoir 53 to a relief valve 59 in the first bypass that is followed by a downstream throttle valve 58. The 2/2-way valve is for delivery of a water jet pulse with preset duration, whereas the relief valve 59 allows generation of a desired pressure level during the bypass phases ÜD1 ÜD2. For this, the relief valve 59 may be set such that, upon reaching a specified pressure, it releases the first bypass duct so that the pressure may be reduced. The relief valve 59 may function as a controller that preferably is controlled by the controller 51. In another aspect, the pressure-pressure flow characteristic curve of the relief valve 59 may be designed such that during passing the valve some pressure declines at the valve. In one embodiment, the relief valve 59 is completely omitted.

Figure 13:
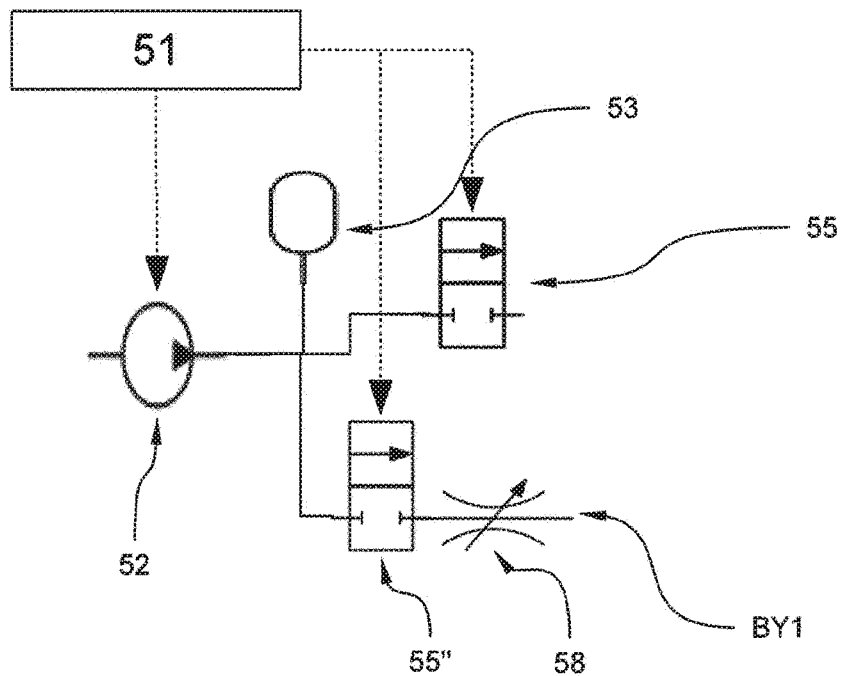
FIG. 13 is a schematic representation of a second alternative design for the creation of a pulsed water jet.

FIG. 13 shows a further illustrating example, wherein two 2/2-way valves are employed. Finally, the first control valve 55 is designed as a 2/2-way valve still serving for controlling proliferation of the pressure present in the system to the application instrument 10. A third control valve—that is as well a 2/2-way valve—allows pressure setting within the system by way of releasing or locking the first bypass BY1. The third control valve 55'' may essentially contribute to building up some excess pressure.

Figure 14:
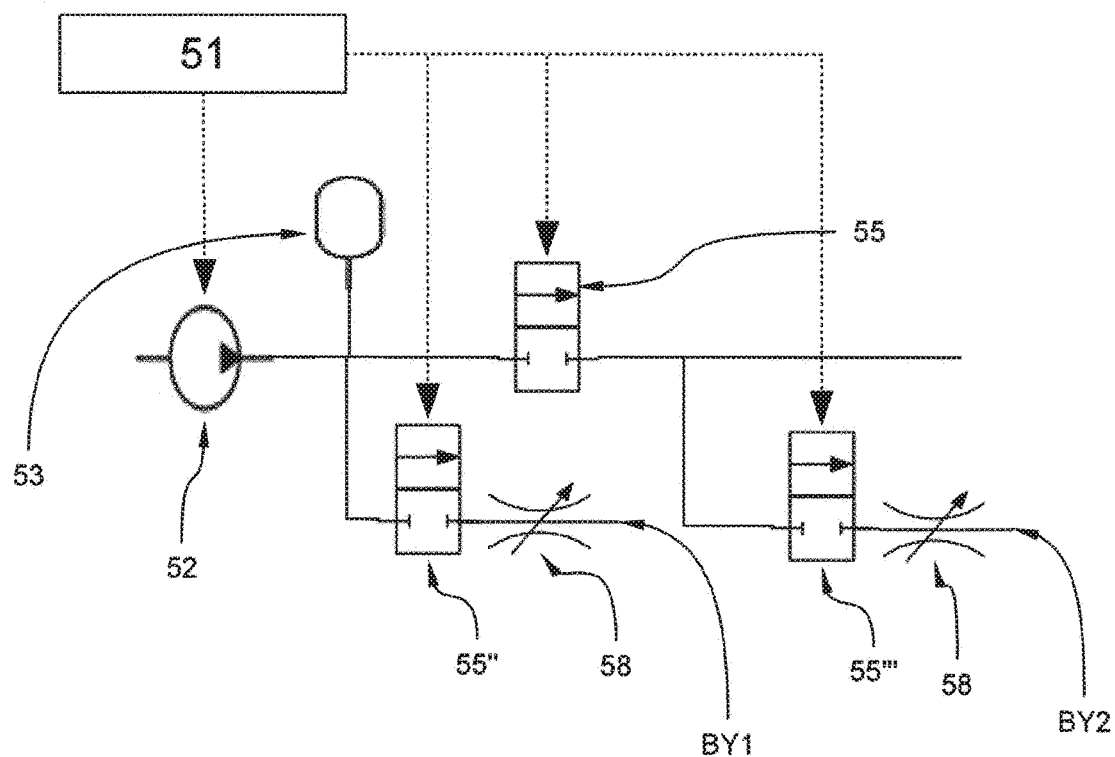
FIG. 14 is a schematic representation of a third alternative design for the creation of a pulsed water jet.
Figure 19:
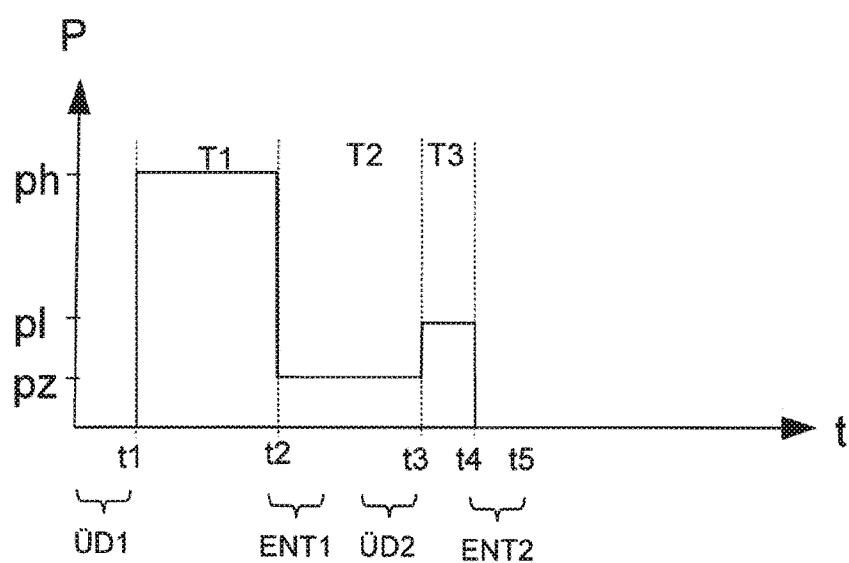
FIG. 19 is a pressure history according to FIG. 18 having additionally indicated bypass and venting phases.

In order to reduce, after delivery of a pulse, the fall time, a further bypass duct BY2 may be provided on the flow-averted side of the first control valve. FIG. 14 shows a respective embodiment of the valve arrangement in an initial state, wherein the valves are controlled according to the application step. A fourth control valve 55''' allows for rapid and specific reduction of the present pressure in the inlets 11, 12'. This embodiment allows realization of venting phases ENT1, ENT2, as it is shown in FIG. 19. In the embodiment shown in FIG. 14 is thus possible to build up excess pressure in a first bypass phase ÜD1 and to specifically transfer it to the application instrument 10 so that, at the nozzle 23 thereof, a pulse with an edge as steep as possible is emitted. Subsequently, the pump 52 further drives the fluid to maintain the first pressure during the first time interval T1. Subsequently, the first control valve 55 is locked to terminate the pulse (point of time t2). At the same time, the fourth control valve 55''' is opened to create fluid communication with the second bypass duct BY2. In this way, the first venting phase ENT1 is implemented. The fall time is very low leading to direct pressure reduction, for example in the distal reservoir 24. Analogously, during the third time interval T3—application of the suspension—a pulse edge as steep possible at the beginning (bypass phase ÜD2) and at the end (venting phase ENT2) may be achieved.

Figure 15:
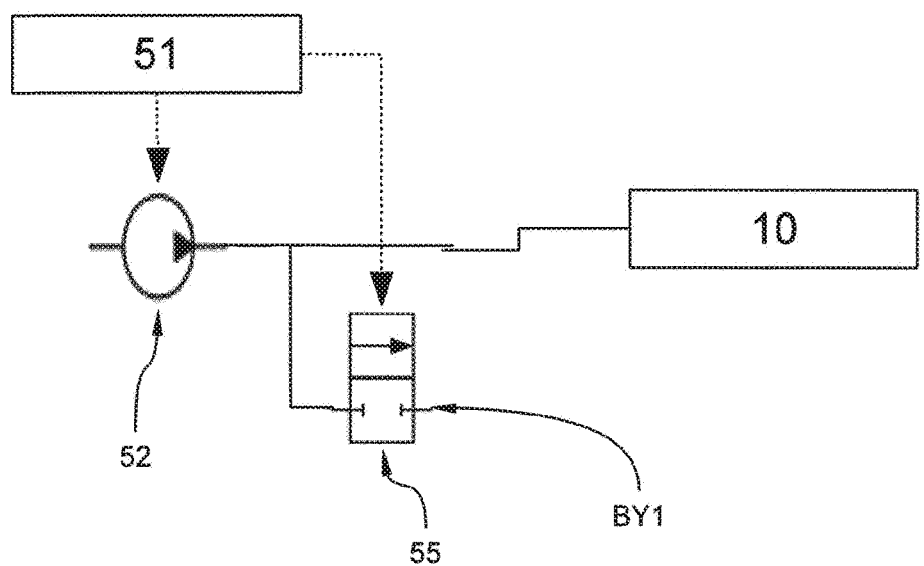
FIG. 15 is a schematic representation of a fourth alternative design for the creation of a pulsed water jet.

FIG. 15 shows an illustrating example, in which a 2/2-way valve is used as first control valve 55. The 2/2-way valve is integrated in the bypass duct BY1, whereas the application instrument 10 is directly connected to the pump. An advantage of this design resides in that with it also venting phases ENT1, ENT2 may be implemented for faster pressure reduction. In comparison to the embodiments previously described this embodiment is very simple and stable.

Figure 16:
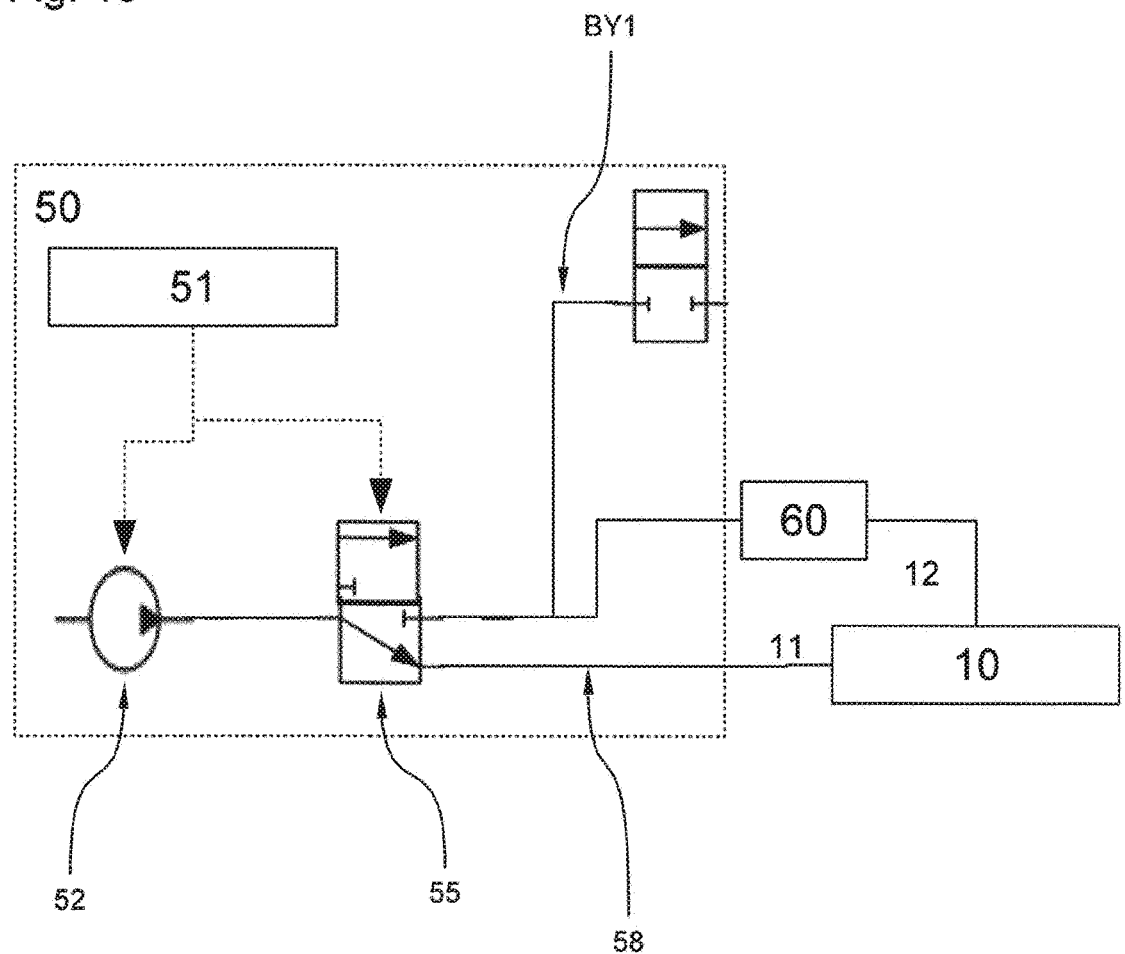
FIG. 16 is a schematic representation of a fifth alternative design for the creation of a pulsed water jet.

FIG. 16 shows a further illustrating example of the supply system 50 according to the invention. Herein, two 3/2-way valves are employed to realize the already described functionality.

The described active valves and control valves, respectively, may have an electromagnetic drive or another drive known in the art. For example, piezo actors, a pneumatic drive unit or analogues may be used. Furthermore, the embodiments may be combined with each other in any manner. For realization of the invention, needle valves, membrane valves, rocker valves and others may be employed. For realization of the described 2/2-way valves for example a clamp valve may be employed, which is preferred due to its sterilisability.

Figure 18:
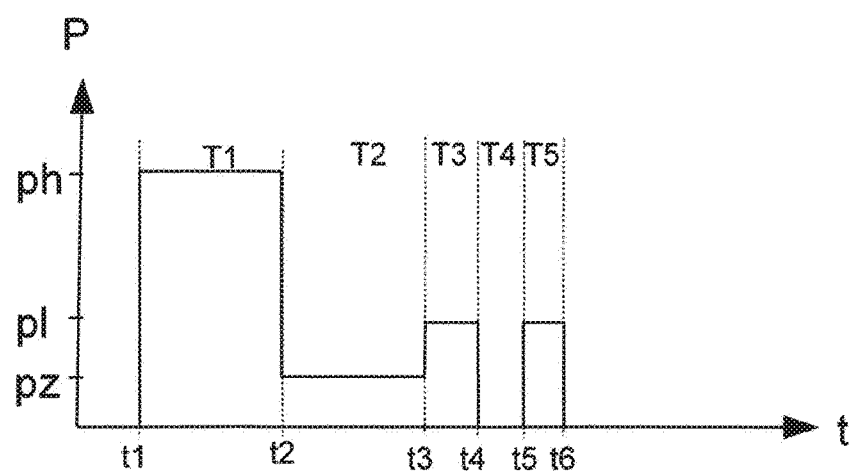
FIG. 18 is a pressure history generated by the supply system according to a second control algorithm.

FIG. 17 and FIG. 18 show different pressure histories, each having a pulse for perforation of the tissue (=first time interval T1) and two pulses for application of the substance (=third and fifth time interval T3 and T5). The second time interval T2 is used to fill the distal reservoir 24. According to FIG. 17, refill of the distal reservoir 24 is done in the fourth time interval T4. According to FIG. 18, a respective refill is omitted.

FIG. 19 shows the time arrangement of the bypass phases BY1, BY2 and of the venting phase ENT1, ENT2 in relation to the time intervals T1 through T5. The first bypass phase terminates with the beginning of the first time interval T1 at the time t1. The first venting phase ENT1 starts at the end of the first time interval T1 at the time t2. In the interval between t2 and t3 the second bypass phase BY2 starts, which terminates at the time t3 with the beginning of the third time interval T3. At the end of the third time interval T3, at the time t4, the second venting phase ENT2 starts, which terminates at the time t5.

LIST OF REFERENCE NUMBERS

1 Mucosa
2 Muscularis
3 Lamina propria
4 Circular muscle
5 Rib
6 Reinforcment fiber
10 Application instrument
11 First inlet, first feed line
12 Second inlet, second feed line
14 Probe shaft
20 Instrument head
21 Internal feed canal
21' First feed canal
22 External feed canal
22' Second feed canal
23 Exit opening, nozzle
24 Distal reservoir
25 Shuttle valve
25 Check valve
26 Side opening
28 Separation wall
30 Flexible tubing
31 Clamp ring
32 Sealing edge
34 First section
35 Second section
36 Third section
40 Venting device
41 Vent
44 Venting chamber
45 Venting valve
50 Supply system
51 Control
52 Pump
53 Pressure reservoir
54 Pressure duct
55, 55' Control valve
58 Throttle valve
59 Relief valve
60 Medium separation device
100 Application system
Ad External diameter
BY1, BY2 Bypass duct
ÜD1, ÜD2 Bypass phase
ENT1, ENT2 Venting phase
t1-t6 Point of time
T1-T5 Time interval
pz, pl, ph Pressure

What is claimed is:

1. A method for injection of liquids with a fluid jet applicator, the method comprising:
creating a canal in a tissue by expelling a first pulse of only a first fluid at a first pressure from a nozzle of the fluid jet applicator into the tissue; and
delivering a first pulse of a second fluid at a second pressure into the canal in the tissue created by the first pulse of the first fluid, wherein the second pressure is lower than the first pressure and the second fluid is different from the first fluid.

2. The method of claim 1, further comprising delivering the first pulse of the second fluid using a second pulse of the first fluid to propel the second fluid.

3. The method of claim 1, wherein the first pressure is at least twice as large as the second pressure.

4. The method of claim 1, further comprising creating the canal and delivering the first pulse of the second fluid into the canal within a time interval of less than two seconds.

5. The method of claim 4, wherein the time interval is less than 1 second.

6. The method of claim 1, wherein the second fluid contains cells.

7. The method of claim 6, wherein the second pressure is a quantity effective to prevent damage to the cells in the second fluid.

8. The method of claim 1, wherein the first pressure is between 40 and 100 bar.

9. The method of claim 1, wherein the first pressure is between 60 and 90 bar.

10. The method of claim 1, wherein the second pressure is between 1 and 40 bar.

11. The method of claim 1, wherein the second pressure is between 2 and 20 bar.

12. The method of claim 1, wherein the tissue is a gastrointestinal wall, and delivering the first pulse of the second fluid into the canal includes delivering the first pulse of the second fluid to a muscularis.

13. The method of claim 1, further comprising delivering a second pulse of the second fluid at a third pressure into the canal in the tissue created by the first pulse of the first fluid, wherein the third pressure is lower than the first pressure.

14. The method of claim 1, further comprising raising a pressure of the first fluid prior to expelling the first pulse of the first fluid at the first pressure.

15. The method of claim 14, further comprising operating a pump fluidly connected with the fluid jet applicator with a control valve downstream of the pump in a closed configuration to raise the pressure of the first fluid prior to expelling the first pulse of the first fluid; and opening the control valve to expel the first pulse of the first fluid at the first pressure.

16. The method of claim 1, further comprising terminating the first pulse of the first fluid by closing a control valve fluidly connected with the fluid jet applicator.

17. The method of claim 16, further comprising opening a bypass downstream of the control valve to reduce a pressure of the first fluid within the fluid jet applicator.

18. The method of claim 1, further comprising, after expelling the first pulse of the first fluid, lowering a pressure of the first fluid prior to delivering the first pulse of the second fluid at the second pressure.

* * * * *